(12) United States Patent
Malone et al.

(10) Patent No.: US 11,344,826 B2
(45) Date of Patent: May 31, 2022

(54) MACHINE FLUID SYSTEM HAVING FILTER PROTECTOR FOR SOCK FILTER IN MANIFOLD TUBE ASSEMBLY

(71) Applicant: Caterpillar Inc., Deerfield, IL (US)

(72) Inventors: Kevin Edwin Malone, Germantown Hills, IL (US); Shawn Richard Herold, East Peoria, IL (US); Theron James Cassidy, Peoria, IL (US); Matthew Fahrenkrug, Chillicothe, IL (US); Dustin Irvin Landwehr, Kewanee, IL (US)

(73) Assignee: Caterpillar Inc., Peoria, IL (US)

( * ) Notice: Subject to any disclaimer, the term of this patent is extended or adjusted under 35 U.S.C. 154(b) by 485 days.

(21) Appl. No.: 16/374,349

(22) Filed: Apr. 3, 2019

(65) Prior Publication Data

US 2020/0316500 A1    Oct. 8, 2020

(51) Int. Cl.
| | |
|---|---|
| *B01D 29/27* | (2006.01) |
| *B01D 35/027* | (2006.01) |
| *B01D 35/30* | (2006.01) |
| *C12M 1/00* | (2006.01) |

(52) U.S. Cl.
CPC ........... *B01D 29/27* (2013.01); *B01D 35/027* (2013.01); *B01D 35/306* (2013.01); *B01D 2201/301* (2013.01); *C12M 23/14* (2013.01); *C12M 23/26* (2013.01); *C12M 29/04* (2013.01)

(58) Field of Classification Search
CPC ............................ B01D 29/27; B01D 35/306; B01D 2201/301; F01N 2610/02; F01N 2610/10; F01N 2610/1406; F01N 2610/1426

See application file for complete search history.

(56) References Cited

U.S. PATENT DOCUMENTS

| | | |
|---|---|---|
| 8,459,013 B2 | 6/2013 | Hosaka et al. |
| 9,308,475 B2 | 4/2016 | Badeau et al. |
| 9,376,655 B2 | 6/2016 | Larsen et al. |
| 9,376,950 B2 | 6/2016 | Servante et al. |
| 2015/0089996 A1 | 4/2015 | Reimer et al. |
| 2015/0198071 A1 | 7/2015 | Hudgens et al. |
| 2017/0014739 A1 | 1/2017 | Roesgen et al. |
| 2017/0122170 A1* | 5/2017 | Fahrenkrug ........ B01D 35/0276 |
| 2017/0189837 A1 | 7/2017 | Herold et al. |
| 2017/0328745 A1 | 11/2017 | Kruse et al. |
| 2018/0016957 A1 | 1/2018 | Woods et al. |

FOREIGN PATENT DOCUMENTS

| | | |
|---|---|---|
| CN | 204851392 | 12/2015 |
| EP | 3168439 | 3/2019 |

* cited by examiner

*Primary Examiner* — Patrick Orme
(74) *Attorney, Agent, or Firm* — Brannon Sowers & Cracraft

(57) ABSTRACT

A fluid system for a machine includes a tube assembly and a sock filter enveloping the tube assembly. The fluid system also includes a filter protector adjacent to a fastener in the tube assembly and including a first connector fitted with a first tube, a second connector fitted with a second tube, and a wall that arcs between the first connector and the second connector and limits contact between a sock filter enveloping the tube assembly and the fastener.

19 Claims, 5 Drawing Sheets

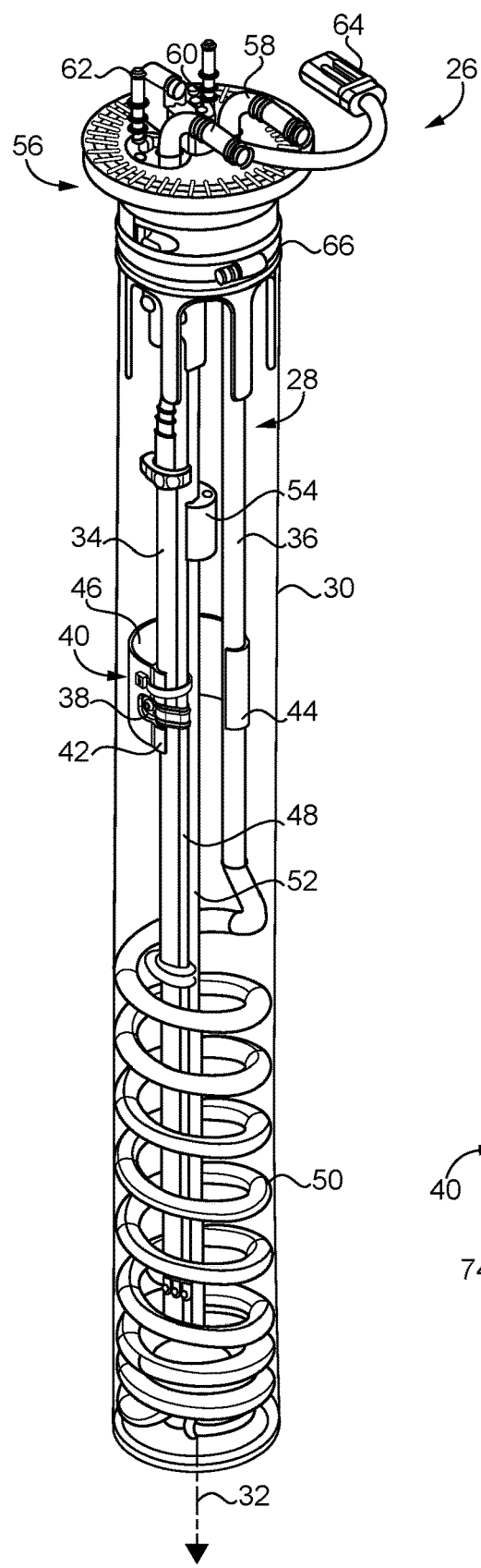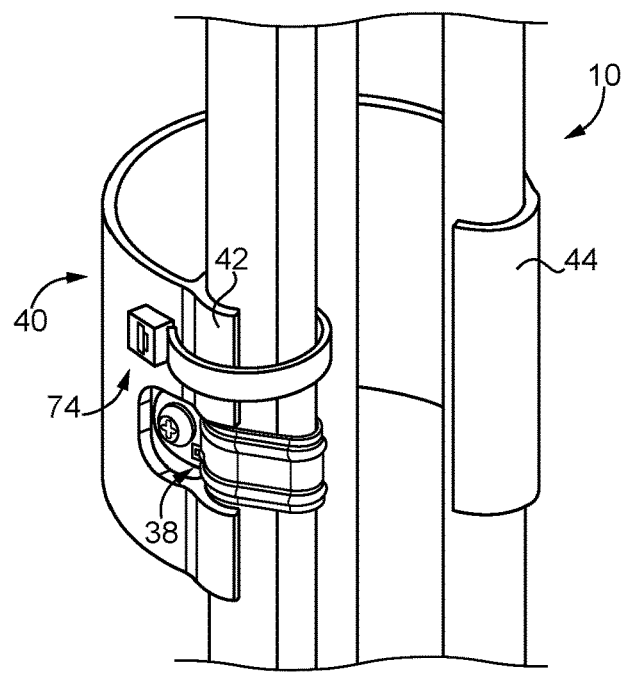
FIG. 2
FIG. 3

US 11,344,826 B2

MACHINE FLUID SYSTEM HAVING FILTER PROTECTOR FOR SOCK FILTER IN MANIFOLD TUBE ASSEMBLY

TECHNICAL FIELD

The present disclosure relates generally to a fluid system in a machine, and more particularly to a filter protector in a fluid system for limiting contact between a sock filter and a fastener in a tube assembly.

BACKGROUND

A great many fluid systems are used in machines ranging from fuel systems to lubrication systems, temperature control systems and many others. One known fluid system used for controlling certain internal combustion engine emissions in machines is coupled to the machine's exhaust system and delivers a reductant for catalytic reduction of nitrogen oxides. In one typical system, a fluid reductant, commonly referred to as diesel exhaust fluid (DEF) or by similar terms, includes a urea-based aqueous solution that is injected into a stream of exhaust gas from the internal combustion engine upstream of a catalytic reduction module. The injected DEF produces ammonia that reacts to reduce nitrogen oxides in the exhaust at a catalyst according to well-known pathways to produce nitrogen gas and water.

Various reductant delivery systems are known and used in a number of different machine applications, notably mobile vehicles in the nature of off-highway machinery and on-highway trucks. The machine carries a fluid tank storing reductant, commonly DEF as noted above, which is delivered in prescribed amounts to the engine exhaust system. It is common for the tank in reductant delivery systems of this general type to be refilled with DEF fluid periodically, and not uncommonly as much as once per day depending on the manner and extent to which the machine is operated. One known reductant delivery system is set forth in United States Patent Publication No. 2017/0122170 to Fahrenkrug, et al. In Fahrenkrug, a fluid reservoir for accommodating a fluid reductant used in a selective catalytic reduction (SCR) exhaust treatment process includes a bag filter to filter debris and contaminants from the reductant prior to being conveyed to the exhaust system for delivery therein.

SUMMARY OF THE INVENTION

In one aspect, a fluid system for a machine includes a tank, and a tube assembly positioned at least partially within the tank. The tube assembly defines a longitudinal center axis and includes a first tube, a second tube, and a fastener attached to the first tube. The first tube and the second tube are offset from one another in a circumferential direction about the longitudinal center axis. The fluid system further includes a sock filter enveloping the tube assembly, and a filter protector positioned adjacent to the fastener. The filter protector includes a first connector fitted with the first tube, a second connector fitted with the second tube, and a wall that arcs about the longitudinal center axis between the first connector and the second connector and limits contact between the sock filter and the fastener.

In another aspect, a filter protector for a tube assembly in a fluid system includes a one-piece protector body having a first connector, a second connector, and a body wall defining a body center axis. The body wall arcs about the body center axis in a circumferential direction between the first connector and the second connector, and extends in an axial direction between a first axial body end and a second axial body end. The first connector extends in the axial direction between the first axial body end and the second axial body end, and has an inner connector wall and an outer connector wall together forming a first tube channel for fitting the first connector with a first tube in the tube assembly. The second connector extends in the axial direction between the first axial body end and the second axial body end, and has an inner connector wall and an outer connector wall together forming a second tube channel for fitting the second connector with a second tube in the tube assembly. The first connector defines a first center opening direction that advances outwardly from the first tube channel and is clear of the one-piece protector body. The second connector defines a second central opening direction that advances outwardly from the second tube channel and intersects the one-piece protector body.

In still another aspect, a filter protector system for a fluid system in a machine includes a filter protector having a one-piece protector body with a first connector, second connector, and a body wall defining a body center axis. The body wall arcs about the body center axis in a circumferential direction between the first connector and the second connector, and extends in an axial direction between a first axial body end and a second axial body end. The first connector extends in the axial direction between the first axial body end and the second axial body end, and has an inner connector wall and an outer connector wall together forming a first tube channel, for fitting the first connector with a first tube in the fluid system. The second connector extends in the axial direction between the first axial body end and the second axial body end, and has an inner connector wall and an outer connector wall together forming a second tube channel, for fitting the second connector with a second tube in the fluid system. The first connector defines a first central opening direction and the second connector defines a second central opening direction, and the one-piece protector body defines a third central opening direction that forms a smaller angle with the first opening direction and a larger angle with the second opening direction.

BRIEF DESCRIPTION OF THE DRAWINGS

FIG. 2 is a diagrammatic view of a manifold assembly for a fluid system, according to one embodiment;

FIG. 3 is an enlarged view of a portion of the manifold assembly of FIG. 2;

DETAILED DESCRIPTION

Figure 1:
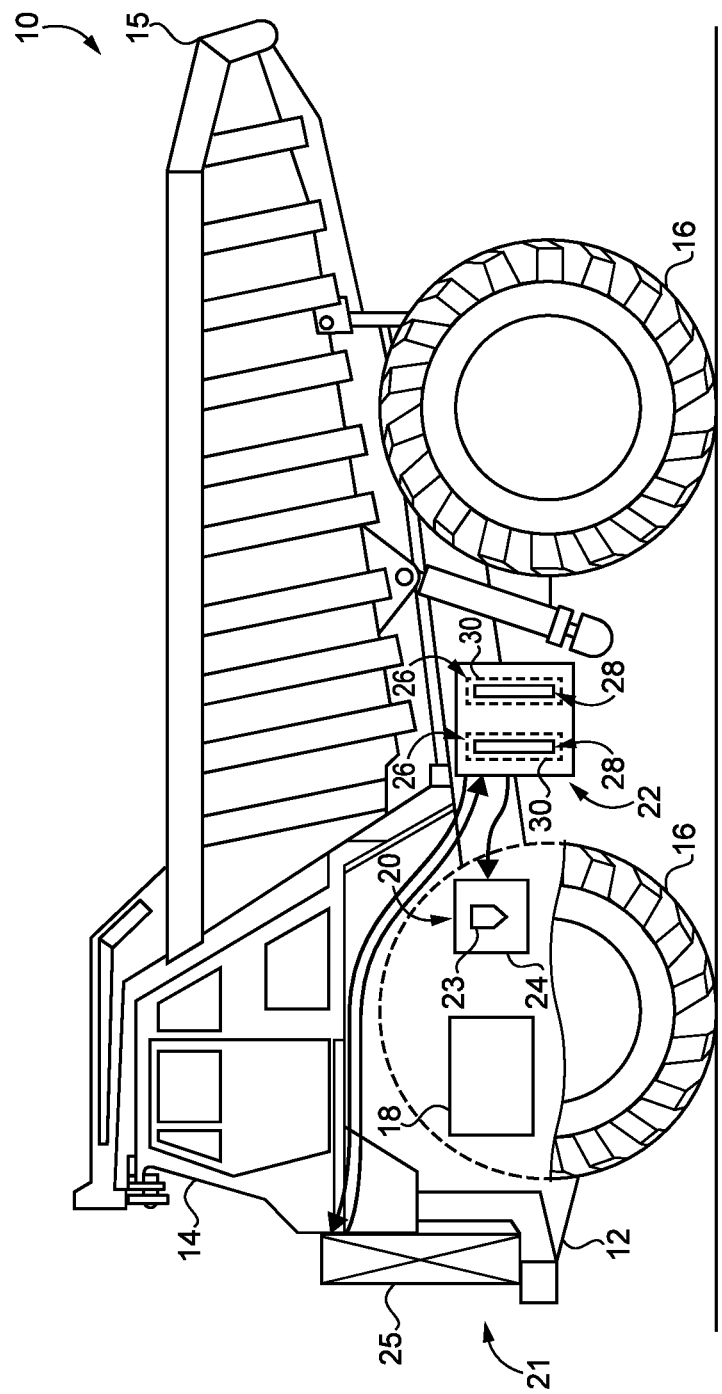
FIG. 1 is a side diagrammatic view of machine, according to one embodiment.

Referring to FIG. 1, there is shown a machine 10 according to one embodiment, and including a frame 12 with a cab 14 and a dump bed 15 mounted thereon. Machine 10 includes a plurality of ground-engaging elements 16, in the illustrated case ground-engaging wheels. Machine 10 also includes an internal combustion engine 18, such as a compression ignition diesel engine, coupled with an exhaust system 20. A temperature control system or cooling system 21 is provided and includes a radiator 25 mounted at a front end of frame 12. Machine 10 is shown in the context of a mining truck, however, the present disclosure is not thereby limited and a variety of on-highway or off-highway machines could benefit by application of the present disclosure, including trucks, tractors, excavators, backhoes, and many others. Machine 10 is also not limited to a mobile machine application, and could be a stationary machine application such as a generator set or genset, a compressor, a pump, or still others.

Machine 10 also includes a fluid system 22 coupled with exhaust system 20 and also with temperature control system 21. Fluid system 22 can include a diesel emission fluid (DEF) system structured to provide a reductant in a liquid form to exhaust system 20 for delivery by way of a DEF admission valve or injector 23 in a generally known manner. No particular type of fluid reductant is intended by way of the present description. Fluid system 22 also includes a tank 24 structured to store DEF. Fluid conduits (not numbered) extend between tank 24 for conveying a temperature control fluid, such as engine coolant, between tank 24 and radiator 25 or other elements of temperature control system 21. In one implementation, warmed engine coolant is conveyed between tank 24 and radiator 25 or other parts of cooling system 21 to warm DEF stored in tank 24 at cold start. Temperature control fluid circulated through tank 24 will be fluidly separated from DEF stored therein. A separate fluid connection can extend between tank 24 and DEF injector 23.

Fluid system 22 also includes a plurality of manifold assemblies 26 positioned at least partially within tank 24. Each manifold assembly 26, hereinafter referred to in the singular, includes a tube assembly 28 positioned at least partially within tank 24, and a sock filter 30 enveloping tube assembly 28. A variety of sock filters are known and commercially available. Sock filter 30 has a flexible form generally akin to a sock or a bag, and can be slipped over one end of tube assembly 28 and secured near or at an opposite end of tube assembly 28 to filter debris and particulates from DEF stored in tank 24 prior to delivery to DEF injector 23. Other fluid systems could employ different plumbing, valves, injectors, admission mechanisms, or other hardware from that described herein. As will be further apparent from the following description, fluid system 22 is uniquely configured to eliminate or retard wear of sock filter 30 that might otherwise lead to admission of debris or particulates into other parts of fluid system 22 that can result in performance degradation.

Figure 4:
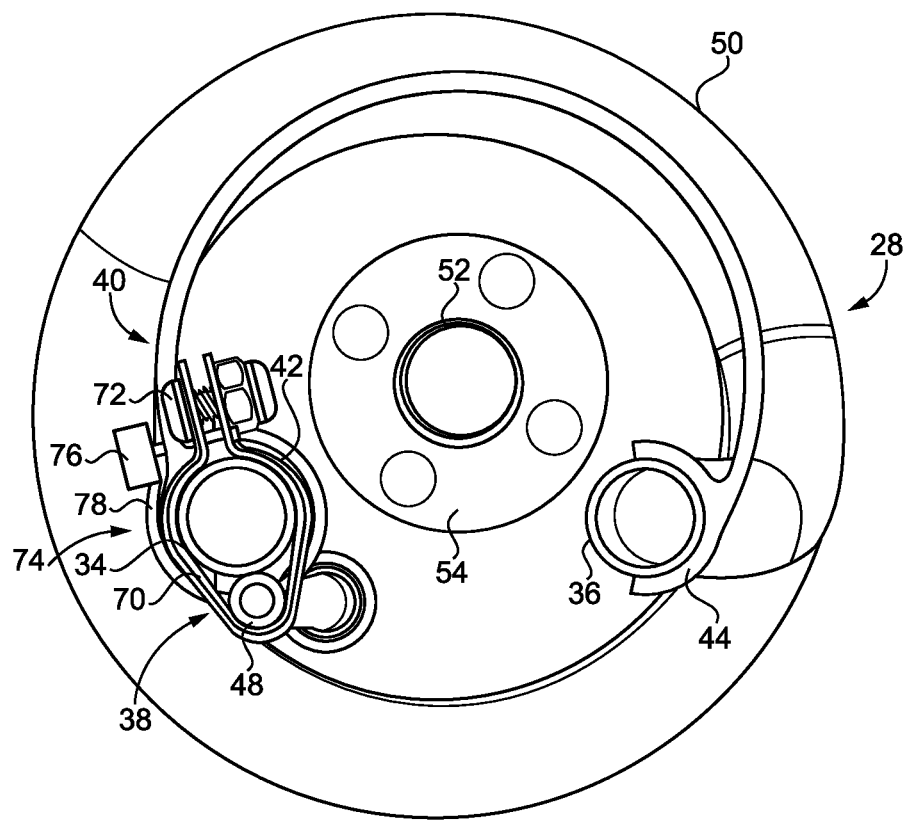
FIG. 4 is an axial section view through a tube assembly, according to one embodiment.

Referring also now to FIGS. 2-4, there are shown additional details of manifold assembly 26. Tube assembly 28 defines a longitudinal center axis 32, and may include a first tube 34, a second tube 36, and a fastener 38 attached to first tube 34. First tube 34 and second tube 36 are offset from one another in a circumferential direction about longitudinal center axis 32. Fluid system 22 also includes a filter protector 40 positioned adjacent to fastener 38 and including a first connector 42 fitted with first tube 34, a second connector 44 fitted with second tube 36, and a wall 46 that arcs about longitudinal center axis 32 between first connector 42 and second connector 44 and limits contact between sock filter 30 and fastener 38. First connector 42 and second connector 44 may be shaped complimentary to first tube 34 and second tube 36, as further discussed herein.

Manifold assembly 26 further includes a header piece 56 and a plurality of coolant connectors 58 and 60 mounted to header piece 56 and structured to convey coolant to and from temperature control system 21. It has been discovered that cold temperatures at startup of machine 10 can be associated with frozen or partially frozen DEF, and thus once engine 18 is started warmed engine coolant can be circulated through tank 24 to thaw the DEF therein. One or more DEF connectors may also be provided for conveying DEF, or another fluid stored in intake 24, to a target location in machine 10. Manifold assembly 26 also includes a plug 64 such as an electrical plug for establishing data and electrical power communications between manifold assembly 26 and an onboard electrical system in machine 10. A band clamp 66 may be provided to clamp sock filter 30 to header piece 56.

As noted above, fluid system 22 could be a variety of different fluid systems for a machine. In a diesel emission fluid system implementation, tube assembly 28 may further include a DEF intake tube 48 extending in parallel with first tube 34 and second tube 36, for conveying filtered DEF out of tank 24. Tube assembly 28 may further include a helical tube section 50 connecting first tube 34 to second tube 36, to form a fluid circuit for conveying the temperature control fluid through tank 24. Tube assembly 28 may still further include a sensor tube 52 extending in parallel with first tube 34 and second tube 36 and axially through helical tube section 50, A sensor float 54 is slidable upon sensor tube 52 in an axial direction relative to first tube 34, second tube 36, and intake tube 48. Sensor float 54 can include a magnet, for instance, whose position or movement can be monitored by a sensing apparatus in sensor tube 52. Fastener 38 can include a clamp 70 clamping first tube 34 to intake tube 48, fastener 38 may also include a bolt 72 coupled with a nut to engage clamp 70 around first tube 34 and intake tube 48.

It should be appreciated that the tube assembly composition and arrangement could differ significantly from that disclosed and illustrated. In other instances, a different number of tubes, a different shape of tubes, or different functional purposes than those described could be employed. For instance, fastener 38 might clamp first tube 34 to a different structure in manifold assembly 26, or fastener 38 might not be a clamp at all. It can be noted from FIG. 2 in particular that fastener 38 is positioned approximately midway between opposite axial ends of tube assembly 28 and sock filter 30. It will also be understood that sock filter 30 is soft and generally stretchy and deformable to an extent that the sloshing of liquid, negative or positive pressure changes, inclination of machine 10, or still other factors could result in sock filter 30 impinging upon fastener 38 but for filter protector 40. It has been observed in certain earlier systems that snagging or rubbing or another form of impingement of a sock filter upon a fastener could lead to a hole. While generally more broadly applicable, filter protector 40 may be specially shaped and adapted for protecting sock filter 30 from such a wear phenomenon.

Figures 5, 6:
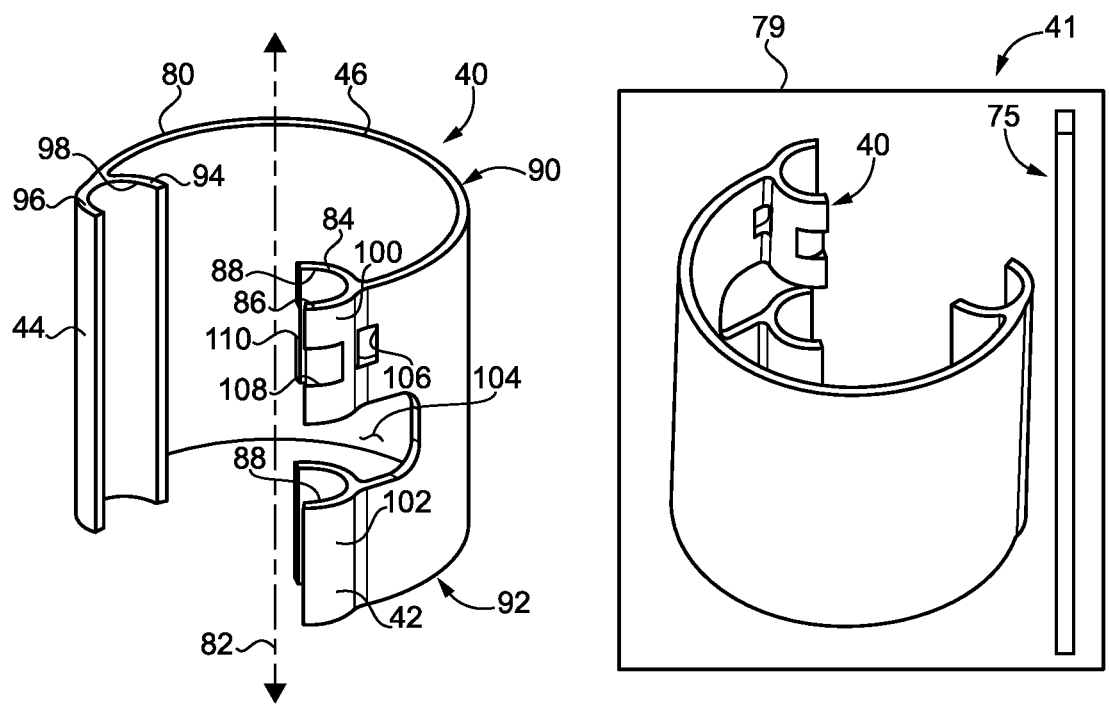
FIG. 5 is a perspective view of a filler protector, according to one embodiment.
FIG. 6 is a diagrammatic view of a packaged filter protector system, according to one embodiment.

Referring also now to FIG. 5, there are shown features of filter protector 40 in further detail. Filter protector 40 includes a one-piece protector body 80 having a first connector 42, a second connector 44, and a body wall 46 defining a body center axis 82. Body wall 46 arcs about body center axis 82 in a circumferential direction between first connector 42 and second connector 44. Body wall 46 extends in an axial direction between a first axial body end 90 and a second axial body end 92. First axial body end 90 is formed in part upon each of first connector 42, second connector 44, and body wall 46, as is second axial body end 92. First connector 42 extends in the axial direction between first axial body end 90 and second axial body end 92, and has an inner connector wall 84 and an outer connector wall 86 together forming a first tube channel 88 for fitting first connector 42 with a first tube in a tube assembly, for example first tube 34 in tube assembly 28. Second connector 44 extends in the axial direction between first axial body end 90 and second axial body end 92, and has an inner connector wall 94 and an outer connector wall 96 together forming a second tube channel 98 for filling second connector 44 with a second tube in a tube assembly, such as second tube 36 in tube assembly 28. Each of tube channels 88 and 98 may have an arcuate shape in an axial cross section through filter protector 40.

First connector 42 may include an upper connector section 100 and a lower connector section 102, each forming a part of first tube channel 88. A slot 104 is formed between upper connector section 100 and lower connector section 102. Slot 104 receives at least a part of fastener 38, and in the illustrated embodiment receives part of bolt 72 and part of clamp 70, with body wall 46 and outer connector wall 86 being positioned generally radially outward of portions of fastener 38. Accordingly, when sock filter 30 is deformed to approach tube assembly 28, filter protector 40 will shield fastener 38 and generally inhibit contact between fastener 38 and sock filter 30. It will be appreciated that filter protector 40 may have other protective functions relative to other parts of tube assembly 28, such as protection against sock filter 30 contacting sensor float 54 or still other components. Moreover, the shape, dimensions, and proportions of filter protector 40 can assist in protecting sock filter 30 from contact with parts of tube assembly 28 by means different than obscuring fastener 38 within a slot 104. Filter protector 40 will typically fit with a spatial envelope of tube assembly 28 defined, axially, by an axial length of the several tubes and, circumferentially, by a diameter of helical tube section 50.

Filter protector 40 may also include a tie-hole 106 that extends through body wall 46 at a location adjacent to first connector 42. Tie-hole 106 is shown axially between slot 104 and first axial body end 90, however, other locations are contemplated. Tie-hole 106 is, more particularly, illustrated as located adjacent to upper connector section 100. Upper connector section 100 includes a first tie channel 108 formed in inner connector wall 84 and a second tie channel 110 formed in outer connector wall 86. First tie channel 108, second tie channel 110, and tie-hole 106 together define a tie path for routing a tie such as a zip tie circumferentially around upper connector section 100 and first tube 34. Slot 104 is formed axially between upper connector section 100 and lower connector section 102 and in part within body wall 54. Tie 74 can include a zip tie as noted above, and includes a head 76 and a strap 78. Tie 74 could include a metallic zip tie, such as a steel zip tie in one embodiment, and will otherwise typically be formed from a DEF-compatible material. Referring to FIG. 6, there is shown filter protector 40 as it might appear in a filter protector system 41 provided as a machine or fluid system service package. Filter protector system 41 includes filter protector 40, tie 75, and a package 79 such as a box or envelope, and can be provided as a service package for installation of filter protectors in a field population of machines.

Figure 7:
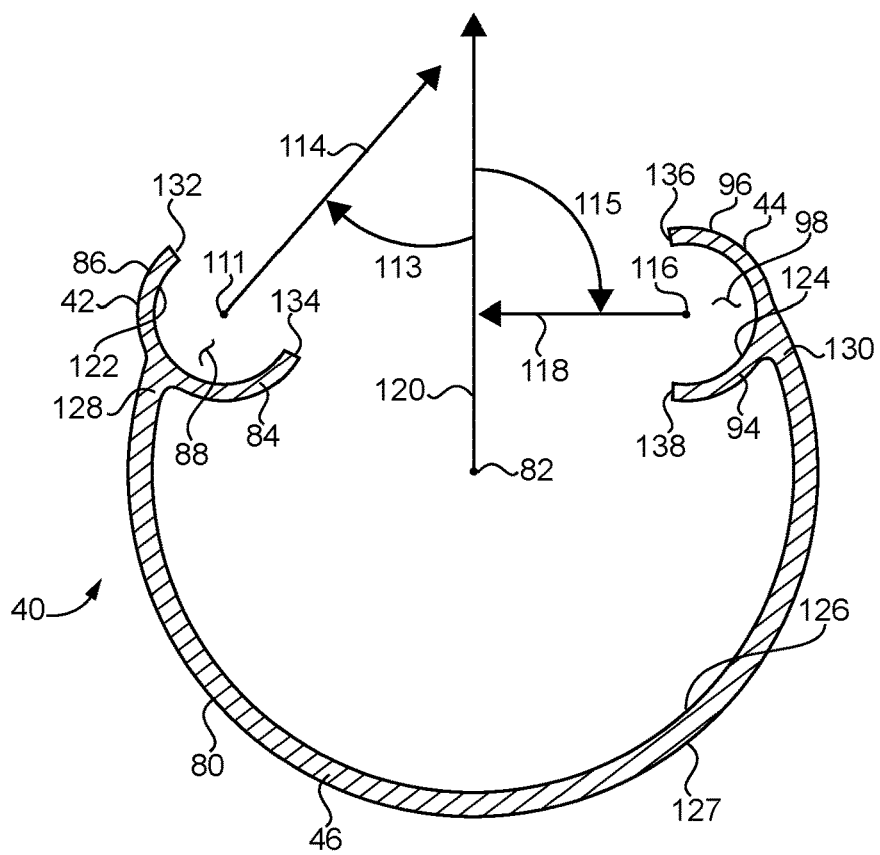
FIG. 7 is an axial section view through a filter protector, according to one embodiment.

Referring now to FIG. 7, there is shown a sectioned view through filter protector 40. Filter protector 40 may be a molded, non-metallic and DEF-compatible component formed, for example, of a glass-filled nylon composite material including integrally molded glass fibers within a nylon matrix. Body wall 46 has an inner arcuate surface 126, an outer arcuate surface 127, and a generally uniform wall thickness throughout. Inner arcuate surface 126 may have a uniform radius of curvature, for example a radius of curvature of about 30 millimeters in one embodiment. As used herein, the term "about" should be understood in the context of conventional rounding to a consistent number of significant digits. Accordingly, "about 30" means from 29.5 to 30.4, and so on. First connector 42 may have an inner arcuate surface 122 having a radius of curvature of about 5 millimeters. Second connector 44 may have an inner arcuate surface 124 having a radius of curvature of about 6 millimeters. Body wall 46 has a first wall end 128 and a second wall end 130. First connector 42 is adjoining to first wall end 128, whereas second connector 44 is adjoining to second wall end 130. Inner connector wall 84 has a wall tip 134 and outer connector wall 86 has a wall tip 132. Inner connector wall 94 has a wall tip 138 and outer connector wall 96 has a wall tip 136. First connector 42 defines a first channel axis 111, which may be the centerpoint of a circle defined by inner arcuate surface 122. Second connector 44 defines a second channel axis 116 that may be a centerpoint of a circle defined by inner arcuate surface 124. Body center axis 82 may be a center of a circle defined by body wall 46. It can be noted that body wall 46 has a C-shape, and each of first connector 42 and second connector 44 has a c-shape adjoining one of the tips of the C-shape, in this case the tips of the C-shape being wall ends 128 and 130. It can further be noted that orientations of the c-shapes formed by first connector 42 and second connector 44 are asymmetric relative to a circle defined by body wall 46. First connector 42 and second connector 44 may thus have orientations in space that are not mirror images, about a plane bisecting body wall 46 and inclusive of body center axis 82, with first connector 42 rotated relatively more outwardly than second connector 44. This general configuration can enable filter protector 40 to be readily installed on tube assembly 28 in a manner that mates with tube assembly 28 and positions body wall 46 to prevent undesired deformation and contact of sock filter 30 with parts of tube assembly 28, as discussed herein.

Another way to understand this aspect of the geometry of filter protector 40, is that first connector 42 defines a first central opening direction 114 that advances outwardly from first tube channel 88 and is clear of one-piece protector body 80, while second connector 44 defines a second central opening direction 118 that advances outwardly from second tube channel 98 and intersects one-piece protector body 80. First channel axis 111 may be intersected by first central opening direction 114. Second channel axis 116 may be intersected by second central opening direction 118. A circumferential offset between first channel axis 111 and second channel axis 116, through one-piece protector body 80, is greater than 180°. An angle (not labeled) formed between first central opening direction 114 and second central opening direction 118, in an axial section plane approximately as show in FIG. 7 is less than 90°. One-piece protector body 80 is further understood to define a third central opening direction 120. First central opening direction 114, second central opening direction 118, and third central opening direction 120 are each oriented perpendicular to a center of the respective c-shape/C-shape, and approximately bisects the same. Third central opening direction 120 extends through body center axis 82 and forms a smaller angle 113 with first central opening direction 114 and a larger angle 115 with second central opening direction 118, In the illustrated embodiment, angle 115 is about 90°, and angle 113 is between 30° and 60°.

Figures 8, 9:
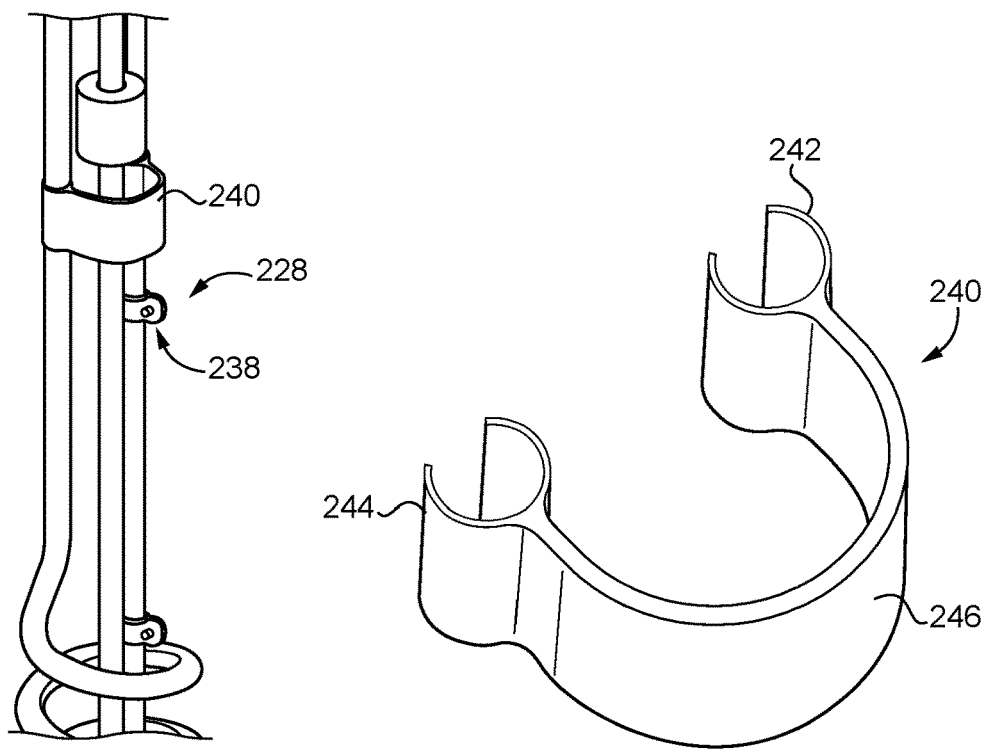
FIG. 8 is a diagrammatic view of a tube assembly, according to one embodiment.
FIG. 9 is a perspective view of a filter protector, according to one embodiment.

Turning now to FIG. 8, there is shown a tube assembly 228 having certain similarities with previously described tube assemblies, including a filter protector 240 and a fastener 238. Fastener 238 and filter protector 240 will be understood to be axially offset from one another, with filter protector 240 being shaped and proportioned to nevertheless limit contact between a sock filter analogous to sock filter 30 and fastener 238. In FIG. 9, filter protector 240 is illustrated including a body wall 246 extending between a first connector 242 and a second connector 244. Body wall 246 can be understood as C-shaped, and first connector 242 and second connector 244 understood as c-shaped. It can also be appreciated that connector 242 and connector 244 have a relatively more closed c-shape than those illustrated in filter protector 40, potentially enabling a relatively more robust interference fit with tubes in tube assembly 228.

Figure 10:
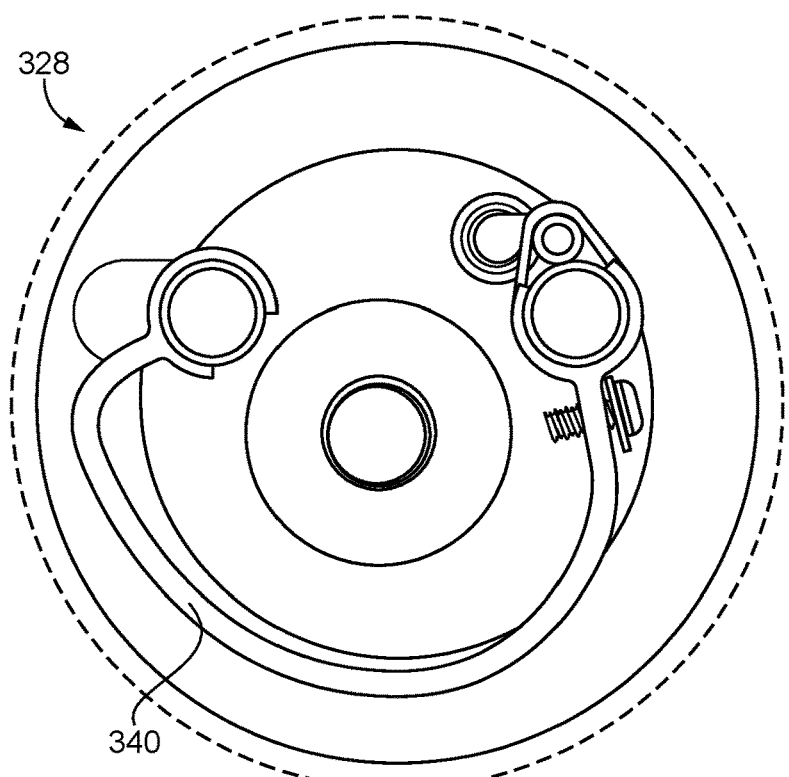
FIG. 10 is an axial section view through a tube assembly, according to one embodiment.
Figure 11:
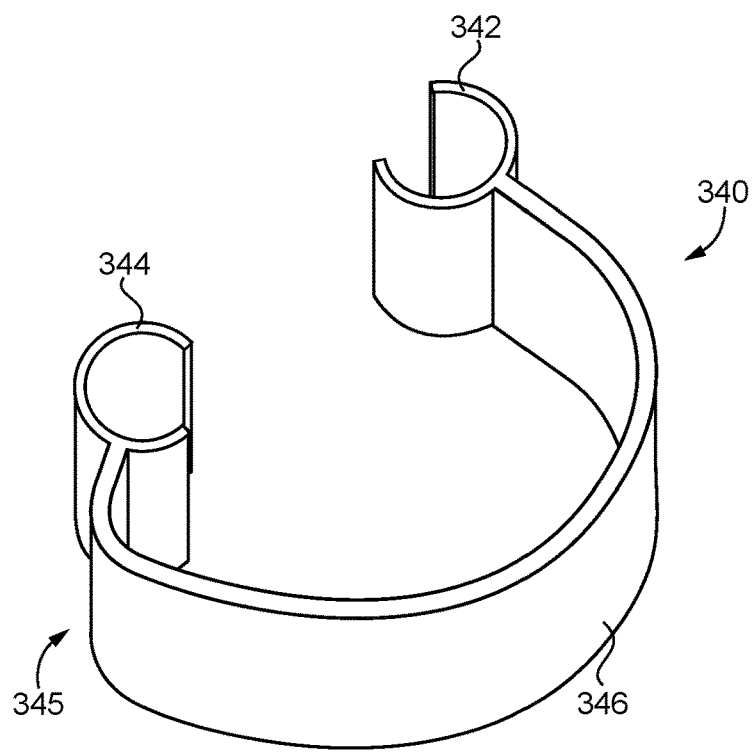
FIG. 11 is a perspective view of a filter protector, according to one embodiment.

FIG. 10 illustrates yet another design where a tube assembly 328 is equipped with a filter protector 340. In FIG. 11 it can be noted that filter protector 340 is not understood as C-shaped, however, a first connector 342 and a second connector 344 can fairly be understood as c-shaped. Filter protector 340 also includes a non-uniform curvature of body wall 346, forming a relatively tighter body curve region 345. It can also be noted that connector 342 and connector 344 are not arranged in a mirror-image symmetrical fashion, in contrast to filter protector 240. In view of the alternative embodiments illustrated in FIGS. 8-11, and other discussed herein, it will be understood that many variations of the general shape of filter protectors according to the present disclosure can be envisioned. In practical implementation strategies, when installed a filter protector is deformed in opposition to a spring bias of at least one of its body wall, its first connector, or its second connector, with the spring bias assisting in keeping the filter protector installed and maintaining an axial positioning in a tube assembly. First connectors and second connectors in the embodiments described could be snap-fitted with their respective tube assemblies, however, it should also be appreciated that elasticity of the body wall may additionally or alternatively assist in retention.

INDUSTRIAL APPLICABILITY

Referring to the drawings generally, it will be recalled that a filter protector according to the present disclosure can be installed in a manifold assembly in the field. A service technician could receive a packaged filter protector system such as filter protector system 41, and when servicing fluid system 22 remove sock filter 30, and clip a filter protector 40, 240, 340 in place. Although not limited as such, in a typical installation pattern, first connector 42, 242, 342 can be fitted with first tube 34, and then filter protector 40, 240, 340 deformed in opposition to a bias of body wall 46 to slip second connector 44, 244, 344 over and around second tube 36 to fit therewith. Prior to or after clipping filter protector 40, 240, 340 in placed, zip tie 75, structured to extend through tie-hole 106, can be passed through tie-hole 106 and fitted within first tie channel 108 and second tie channel 110, and then strap 78 passed through head 76 to complete the securing of filter protector 40 in place.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims. As used herein, the articles "a" and "an" are intended to include one or more items, and may be used interchangeably with "one or more." Where only One item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A fluid system for a machine comprising:
   a tank;
   a tube assembly positioned at least partially within the tank, the tube assembly defining a longitudinal center axis and including a first tube, a second tube, and a fastener attached to the first tube, and the first tube and the second tube are offset from one another in a circumferential direction about the longitudinal center axis;
   a sock filter enveloping the tube assembly and the fastener; and
   a filter protector positioned adjacent to the fastener and including a first connector fitted with the first tube, a second connector fitted with the second tube, and a wall that arcs about the longitudinal center axis between the first connector and the second connector and limits contact between the sock filter and the fastener.

2. The fluid system of claim 1 comprising a diesel emission fluid (DEF) system where the tube assembly further includes a DEF intake tube extending in parallel with the first tube and the second tube.

3. The fluid system of claim 2 wherein the tube assembly further includes:
   a helical tube section connecting the first tube to the second tube, to form a fluid circuit for conveying a temperature control fluid through the tank;
   a sensor tube extending in parallel with the first tube and the second tube and axially through the helical tube section; and
   a sensor float slidable upon the sensor tube in an axial direction relative to the first, second, and third tubes.

4. The fluid system of claim 2 wherein the fastener includes a clamp clamping the first tube to the DEF intake tube.

5. The fluid system of claim 1 wherein the filter protector is deformed in opposition to a spring bias of at least one of the wall, the first connector, or the second connector that biases the respective at least one of the wall, the first connector, or the second connector toward a neutral, unbiased state.

6. The fluid system of claim 5 wherein the wall has a C-shape, and each of the first connector and the second connector has a c-shape adjoining one of the tips of the C-shape formed by the wall.

7. The fluid system of claim 5 wherein the wall has a slot formed therein, and the fastener is positioned at least partially within the slot.

8. The fluid system of claim 7 wherein the first connector includes an upper connector section and a lower connector section, and the slot is formed between the upper connector section and the lower connector section.

9. A filter protector for a tube assembly in a fluid system comprising:
   a one-piece protector body including a first connector, a second connector, and a body wall defining a body center axis, the body wall arcing about the body center axis in a circumferential direction between the first connector and the second connector, and extending in an axial direction between a first axial body end and a second axial body end;

the first connector extending in the axial direction between the first axial body end and the second axial body end, and having an inner connector wall and an outer connector wall together forming a first tube channel for fitting the first connector with a first tube in the tube assembly;

the second connector extending in the axial direction between the first axial body end and the second axial body end, and having an inner connector wall and an outer connector wall together forming a second tube channel for fitting the second connector with a second tube in the tube assembly;

the first connector defining a first central opening direction in a plane perpendicular to the body center axis that advances outwardly from the first tube channel and is clear of the one-piece protector body, such that the first central opening direction does not intersect the one-piece protector body; and the second connector defining a second central opening direction in the plane perpendicular to the body center axis that advances outwardly from the second tube channel and intersects the one-piece protector body.

10. The filter protector of claim 9 wherein the first tube channel defines a first channel axis and the first central opening direction intersects the first channel axis, and the second tube channel defines a second channel axis and the second central opening direction intersects the second channel axis.

11. The filter protector of claim 10 wherein:

a circumferential offset between the first channel axis and the second channel axis, through the one-piece protector body circumferentially around the body center axis, is greater than 180°; and an angle formed between the first central opening direction and the second central opening direction circumferentially around the body center axis is less than 90°.

12. The filter protector of claim 11 wherein the wall has a C-shape and a uniform radius of curvature between the first connector and the second connector, and each of the first connector and the second connector has a c-shape.

13. The filter protector of claim 9 wherein the first connector includes an upper connector section and a lower connector section, and a slot is formed between the upper connector section and the lower connector section.

14. The filter protector of claim 13 wherein a tie-hole extends through the body wall at a location adjacent to the first connector.

15. The filter protector of claim 14 wherein the tie hole is located adjacent to the upper connector section, and wherein the upper connector section includes a first tie channel formed in the inner connector wall and a second tie channel formed in the outer connector wall, and the first tie channel, the second tie channel, and the tie hole together define a tie path for routing a zip tie circumferentially around the upper connector section and the first tube.

16. The filter protector of claim 13 wherein the slot is formed in part between the upper connector section and the lower connector section and in part within the body wall.

17. A filter protector system for a fluid system in a machine comprising:

a filter protector including a one-piece protector body having a first connector, a second connector, and a body wall defining a body center axis, the body wall arcing about the body center axis in a circumferential direction between the first connector and the second connector, and extending in an axial direction between a first axial body end and a second axial body end;

the first connector extending in the axial direction between the first axial body end and the second axial body end, and having an inner connector wall and an outer connector wall together forming a first tube channel, for fitting the first connector about a first tube in the tube assembly;

the second connector extending in the axial direction between the first axial body end and the second axial body end, and having an inner connector wall and an outer connector wall together forming a second tube channel, for fitting the second connector with a second tube in the tube assembly;

the first connector defining a first central opening direction and the second connector defining a second central opening direction, and the one-piece protector body defining a third central opening direction that forms, circumferentially around the body center axis, a smaller angle with the first opening direction and a larger angle with the second opening direction; and a tie hole extends through the wall at a location that is adjacent to the first connector, and further comprising a tie structured to extend through the tie hole for securing the first connector to the first tube, and a package containing the filter protector and the tie.

18. The filter protector system of claim 17 wherein the body wall has a C-shape and a uniform radius of curvature between the first connector and the second connector, and each of the first connector and the second connector has a c-shape.

19. The filter protector system of claim 17 wherein:

the first tube channel defines a first channel axis and the first central opening direction intersects the first channel axis, and the second tube channel defines a second channel axis and the second central opening direction intersects the second channel axis;

a circumferential offset between the first channel axis and the second channel axis, through the one-piece protector body circumferentially around the body center axis, is greater than 180°; and the first connector includes an upper connector section and a lower connector section, and a slot is formed between the upper connector section and the lower connector section.

* * * * *